United States Patent [19]

Dassel et al.

[11] Patent Number: 6,129,875
[45] Date of Patent: *Oct. 10, 2000

[54] PROCESS OF SEPARATING CATALYST FROM OXIDATION MIXTURES

[75] Inventors: Mark W. Dassel, Indianola; Ader M. Rostami; Douglas J. Dudgeon, both of Bainbridge Island; David C. DeCoster, Buckley, all of Wash.; Eustathios Vassiliou, Newark, Del.

[73] Assignee: RPC Inc., Atlanta, Ga.

[*] Notice: This patent is subject to a terminal disclaimer.

[21] Appl. No.: 09/245,156

[22] Filed: Feb. 4, 1999

Related U.S. Application Data

[60] Provisional application No. 60/075,257, Feb. 19, 1998.

[51] Int. Cl.$^7$ .......................... C07C 51/16; C07C 51/31; D01D 1/02; D01D 5/08; D01F 13/00
[52] U.S. Cl. .................. 264/176.1; 528/176; 528/288; 528/308; 528/322; 528/335; 562/413; 562/543
[58] Field of Search ................ 264/176.1; 528/176, 528/288, 308, 322, 335; 562/413, 543

[56] References Cited

U.S. PATENT DOCUMENTS

| | | | |
|---|---|---|---|
| 1,121,532 | 12/1914 | Newberry . | |
| 2,014,044 | 9/1935 | Haswell | 75/17 |
| 2,223,493 | 12/1940 | Loder | 260/537 |
| 2,223,494 | 12/1940 | Loder | 260/586 |
| 2,301,240 | 11/1942 | Baumann et al. | 183/115 |
| 2,439,513 | 4/1948 | Hamblet et al. | 260/533 |
| 2,557,282 | 6/1951 | Hamblet et al. | 260/533 |
| 2,565,087 | 8/1951 | Porter et al. | 260/631 |
| 2,980,523 | 4/1961 | Dille et al. | 48/215 |
| 3,161,603 | 12/1964 | Leyshon et al. | 252/413 |
| 3,231,608 | 1/1966 | Kollar | 260/533 |
| 3,234,271 | 2/1966 | Barker et al. | 260/531 |
| 3,290,369 | 12/1966 | Bonfield et al. | 260/537 |
| 3,361,806 | 1/1968 | Lidov | 260/531 |
| 3,515,751 | 6/1970 | Oberster et al. | 260/533 |
| 3,530,185 | 9/1970 | Pugi | 260/586 |
| 3,613,333 | 10/1971 | Gardenier | 55/89 |
| 3,677,696 | 7/1972 | Bryk et al. | 23/2 |
| 3,839,435 | 10/1974 | Shigeyasu et al. | 260/524 R |
| 3,928,005 | 12/1975 | Laslo | 55/73 |
| 3,932,513 | 1/1976 | Russell | 260/586 |
| 3,946,076 | 3/1976 | Paasen et al. | 260/586 |
| 3,957,876 | 5/1976 | Rapoport et al. | 260/586 |
| 3,987,100 | 10/1976 | Barnette et al. | 260/586 |
| 3,987,808 | 10/1976 | Carbonell et al. | 137/3 |
| 4,025,498 | 5/1977 | Buss et al. | 260/95 A |
| 4,032,569 | 6/1977 | Onopchenko et al. | 260/533 C |
| 4,039,304 | 8/1977 | Bechthold et al. | 55/10 |
| 4,055,600 | 10/1977 | Langley et al. | 260/586 |
| 4,065,527 | 12/1977 | Graber | 261/79 A |
| 4,158,739 | 6/1979 | Schulz et al. | 562/543 |
| 4,160,108 | 7/1979 | Shigeyasu et al. | 562/416 |
| 4,263,453 | 4/1981 | Schulz et al. | 562/543 |
| 4,308,037 | 12/1981 | Meissner et al. | 55/10 |
| 4,332,590 | 6/1982 | Smith | 23/230 A |
| 4,361,965 | 12/1982 | Goumondy et al. | 34/57 R |
| 4,370,304 | 1/1983 | Hendriks et al. | 422/224 |
| 4,394,139 | 7/1983 | Board | 55/20 |
| 4,419,184 | 12/1983 | Backlund | 162/49 |
| 4,423,018 | 12/1983 | Lester, Jr. et al. | 423/243 |
| 4,477,380 | 10/1984 | Knips et al. | 260/385 |
| 4,603,220 | 7/1986 | Feld | 562/416 |
| 5,061,453 | 10/1991 | Krippl et al. | 422/106 |
| 5,104,492 | 4/1992 | King et al. | 203/15 |
| 5,123,936 | 6/1992 | Stone et al. | 55/8 |
| 5,170,727 | 12/1992 | Nielsen | 110/346 |
| 5,221,800 | 6/1993 | Park et al. | 562/543 |
| 5,244,603 | 9/1993 | Davis | 261/87 |
| 5,270,019 | 12/1993 | Melton et al. | 422/234 |

(List continued on next page.)

FOREIGN PATENT DOCUMENTS

| | | |
|---|---|---|
| 439 007 A2 | 7/1991 | European Pat. Off. . |
| 729 084 A1 | 8/1996 | European Pat. Off. . |
| 729 085 A1 | 8/1996 | European Pat. Off. . |
| 751 105 A2 | 1/1997 | European Pat. Off. . |
| 2 722 783 A1 | 1/1996 | France . |
| 4426132 A1 | 1/1996 | Germany . |
| 4427474 | 2/1996 | Germany . |
| 48-003815 | 2/1973 | Japan . |
| 50-034006B | 11/1975 | Japan . |
| 415172 | 8/1934 | United Kingdom . |
| 738808 | 10/1955 | United Kingdom . |
| 864106 | 3/1961 | United Kingdom . |
| 1143213 | 2/1969 | United Kingdom . |
| 2014473 | 8/1979 | United Kingdom . |
| WO 96/03365 | 2/1996 | WIPO . |
| WO 96/14288 | 5/1996 | WIPO . |
| WO 96/40610 | 12/1996 | WIPO . |
| WO 97/49485 | 12/1997 | WIPO . |

OTHER PUBLICATIONS

E. Sorribes et al., "Formación de neuvas fases en el proceso de obstención de ácido adípico: causas y efectos que provocan," *Rev. R. Acad. Cienc. Exactas, Fis. Nat. Madrid* (1987), 81 (1), 233–5 (+ English language translation).

*Primary Examiner*—Leo B. Tentoni
*Attorney, Agent, or Firm*—Seed Intellectual Property Law Group PLLC

[57] ABSTRACT

This invention relates to methods for controlling the oxidation of hydrocarbons to dibasic acids, in the presence of a catalyst and a monobasic acid, by removing the catalyst from the reaction mixture, outside the oxidation zone, after the oxidation has taken place at least partially. Initially, the catalyst is partially precipitated and removed by reducing the water level in the reaction mixture and/or subjecting the reaction mixture to a temperature, at which or over which catalyst precipitates. After the initial partial precipitation of the catalyst, the remaining catalyst is subjected to a thermal treatment, during which at least part of the monobasic acid is removed leaving behind molten dibasic acids, in which, at least a major part of the remaining catalyst is precipitated, and it is removed. A minor part of remaining catalyst is removed by methods, which include but are not limited to ion exchange, precipitation with a base or appropriate salt, and electrodialysis. The precipitated catalyst in the three removal stages may be recycled in miscellaneous ways. The dibasic acid(s) may be removed at least partially before or after any catalyst precipitation stage.

30 Claims, 1 Drawing Sheet

U.S. PATENT DOCUMENTS

| | | | |
|---|---|---|---|
| 5,271,904 | 12/1993 | Esposito et al. | 422/105 |
| 5,286,458 | 2/1994 | Yang et al. | 422/168 |
| 5,294,378 | 3/1994 | Succi et al. | 261/130 |
| 5,312,567 | 5/1994 | Kozma et al. | 261/87 |
| 5,321,157 | 6/1994 | Kollar | 562/543 |
| 5,374,767 | 12/1994 | Drinkard et al. | 560/193 |
| 5,396,850 | 3/1995 | Conochie et al. | 110/346 |
| 5,399,750 | 3/1995 | Brun et al. | 562/553 |
| 5,463,119 | 10/1995 | Kollar | 562/543 |
| 5,502,245 | 3/1996 | Dassel et al. | 562/413 |
| 5,516,423 | 5/1996 | Conoby et al. | 210/85 |
| 5,558,842 | 9/1996 | Vassiliou et al. | 422/108 |
| 5,580,531 | 12/1996 | Vassiliou et al. | 422/108 |
| 5,654,475 | 8/1997 | Vassiliou et al. | 562/413 |
| 5,756,837 | 5/1998 | Constantini et al. | 562/543 |
| 5,801,273 | 9/1998 | Vassiliou et al. | 562/413 |
| 5,801,282 | 9/1998 | Dassel et al. | 562/413 |
| 5,817,868 | 10/1998 | Rostami et al. | 562/413 |
| 5,824,819 | 10/1998 | Dassel et al. | 562/529 |
| 5,908,589 | 6/1999 | DeCoster et al. | 264/176.1 X |

PROCESS OF SEPARATING CATALYST FROM OXIDATION MIXTURES

CROSS-REFERENCE TO RELATED APPLICATION

This application claims the benefit of U.S. Provisional Application No. 60/075,257, filed Feb. 19, 1998, which application is incorporated herein by reference in its entirety.

TECHNICAL FIELD

This invention relates to methods of oxidizing hydrocarbons, such as cyclohexane for example, to respective dibasic acids, such as adipic acid for example, and more specifically, how to remove catalyst after the reaction, preferably for recycling.

BACKGROUND OF THE INVENTION

There is a plethora of references (both patents and literature articles) dealing with the formation of acids, one of the most important being adipic acid, by oxidation of hydrocarbons. Adipic acid is used to produce Nylon 66 fibers and resins, polyesters, polyurethanes, and miscellaneous other compounds.

There are different processes of manufacturing adipic acid. The conventional process involves a first step of oxidizing cyclohexane with oxygen to a mixture of cyclohexanone and cyclohexanol (KA mixture), and then oxidation of the KA mixture with nitric acid to adipic acid. Other processes include, among others, the "Hydroperoxide Process", the "Boric Acid Process", and the "Direct Synthesis Process", which involves direct oxidation of cyclohexane to adipic acid with oxygen in the presence of solvents, catalysts, and promoters.

The Direct Synthesis Process has been given attention for a long time. However, to this date it has found little commercial success. One of the reasons is that although it looks very simple at first glance, it is extremely complex in reality. Due to this complexity, one can find strikingly conflicting results, comments, and views in different references.

It is well known that after a reaction has taken place according to the Direct Synthesis, a mixture of two liquid phases is present at ambient temperature, along with a solid phase mainly consisting of adipic acid. The two liquid phases have been called the "Polar Phase" and the "Non-Polar Phase." However, no attention has been paid so far to the importance of the two phases, except for separating the adipic acid from the "Polar Phase" and recycling these phases to the reactor partially or totally with or without further treatment.

It is also important to note that most studies on the Direct Synthesis have been conducted in a batch mode, literally or for all practical purposes.

As aforementioned, there is a plethora of references dealing with oxidation of organic compounds to produce acids, such as, for example, adipic acid and/or intermediate products, such as for example cyclohexanone, cyclohexanol, cyclohexylhydroperoxide, etc.

The following references, among others, may be considered as representative of oxidation processes relative to the preparation of diacids and other intermediate oxidation products.

U.S. Pat. No. 5,463,119 (Kollar) discloses a process for the oxidative preparation of C5–C8 aliphatic dibasic acids by (1) reacting,
  (a) at least one saturated cycloaliphatic hydrocarbon having from 5 to 8 ring carbon atoms in the liquid phase and
  (b) an excess of oxygen gas or an oxygen-containing gas in the presence of
  (c) a solvent comprising an organic acid containing only primary and/or secondary hydrogen atoms and
  (d) at least about 0.002 mole per 1000 grams of reaction mixture of a polyvalent heavy metal catalyst;
(2) removing the aliphatic dibasic acid; and
(3) recycling intermediates, post oxidation components, and derivatives thereof remaining after removal of the aliphatic dibasic acid into the oxidation reaction.

U.S. Pat. No. 5,374,767 (Drinkard et al.) discloses formation of cyclohexyladipates in a staged reactor, e.g., a reactive distillation column. A mixture containing a major amount of benzene and a minor amount of cyclohexene is fed to the lower portion of the reaction zone and adipic acid is fed to the upper portion of the reaction zone, cyclohexyladipates are formed and removed from the lower portion of the reaction zone and benzene is removed from the upper portion of the reaction zone. The reaction zone also contains an acid catalyst.

U.S. Pat. No. 5,321,157 (Kollar) discloses a process for the preparation of C5–C8 aliphatic dibasic acids through oxidation of corresponding saturated cycloaliphatic hydrocarbons by (1) reacting, at a cycloaliphatic hydrocarbon conversion level of between about 7% and about 30%,
  (a) at least one saturated cycloaliphatic hydrocarbon having from 5 to 8 ring carbon atoms in the liquid phase and
  (b) an excess of oxygen gas or an oxygen containing gas mixture
in the presence of
  (c) less than 1.5 moles of a solvent per mole of cycloaliphatic hydrocarbon (a), wherein said solvent comprises an organic acid containing only primary and/or secondary hydrogen atoms and
  (d) at least about 0.002 mole per 1000 grams of reaction mixture of a polyvalent heavy metal catalyst; and
(2) isolating the C5–C8 aliphatic dibasic acid.

U.S. Pat. No. 3,987,100 (Barnette et al.) describes a process of oxidizing cyclohexane to produce cyclohexanone and cyclohexanol, said process comprising contacting a stream of liquid cyclohexane with oxygen in each of at least three successive oxidation stages by introducing into each stage a mixture of gases comprising molecular oxygen and an inert gas.

U.S. Pat. No. 3,957,876 (Rapoport et al.) describes a process for the preparation of cyclohexyl hydroperoxide substantially free of other peroxides by oxidation of cyclohexane containing a cyclohexane soluble cobalt salt in a zoned oxidation process in which an oxygen containing gas is fed to each zone in the oxidation section in an amount in excess of that which will react under the conditions of that zone.

U.S. Pat. No. 3,932,513 (Russell) discloses the oxidation of cyclohexane with molecular oxygen in a series of reaction zones, with vaporization of cyclohexane from the last reactor effluent and parallel distribution of this cyclohexane vapor among the series of reaction zones.

U.S. Pat. No. 3,530,185 (Pugi) discloses a process for manufacturing precursors of adipic acid by oxidation with an oxygen-containing inert gas which process is conducted in at least three successive oxidation stages by passing a stream of liquid cyclohexane maintained at a temperature in the range of 140° to 200° C. and a pressure in the range of 50 to 350 p.s.i.g. through each successive oxidation stage and by introducing a mixture of gases containing oxygen in each oxidation stage in an amount such that substantially all of the oxygen introduced into each stage is consumed in that stage thereafter causing the residual inert gases to pass countercurrent into the stream of liquid during the passage of the stream through said stages.

U.S. Pat. No. 3,515,751 (Oberster et al.) discloses a process for the production of epsilon-hydroxycaproic acid in which cyclohexane is oxidized by liquid phase air oxidation in the presence of a catalytic amount of a lower aliphatic carboxylic acid and a catalytic amount of a peroxide under certain reaction conditions so that most of the oxidation products are found in a second, heavy liquid layer, and are directed to the production of epsilon-hydroxycaproic acid.

U.S. Pat. No. 3,361,806 (Lidov et al.) discloses a process for the production of adipic acid by the further oxidation of the products of oxidation of cyclohexane after separation of cyclohexane from the oxidation mixture, and more particularly to stage wise oxidation of the cyclohexane to give high yields of adipic acid precursors and also to provide a low enough concentration of oxygen in the vent gas so that the latter is not a combustible mixture.

U.S. Pat. No. 3,234,271 (Barker et al.) discloses a process for the production of adipic acid by the two-step oxidation of cyclohexane with oxygen. In a preferred embodiment, mixtures comprising cyclohexanone and cyclohexanol are oxidized. In another embodiment, the process involves the production of adipic acid from cyclohexane by oxidation thereof, separation of cyclohexane from the oxidation mixture and recycle thereof, and further oxidation of the other products of oxidation.

U.S. Pat. No. 3,231,608 (Kollar) discloses a process for the preparation of aliphatic dibasic acids from saturated cyclic hydrocarbons having from 4 to 8 cyclic carbon atoms per molecule in the presence of a solvent which comprises an aliphatic monobasic acid which contains only primary and secondary hydrogen atoms and a catalyst comprising a cobalt salt of an organic acid, and in which process the molar ratio of said solvent to said saturated cyclic hydrocarbon is between 1.5:1 and 7:1, and in which process the molar ratio of said catalyst to said saturated cyclic hydrocarbon is at least 5 millimoles per mole.

U.S. Pat. No. 3,161,603 (Leyshon et al.) discloses a process for recovering the copper-vanadium catalyst from the waste liquors obtained in the manufacture of adipic acid by the nitric acid oxidation of cyclohexanol and/or cyclohexanone.

U.S. Pat. No. 2,565,087 (Porter et al.) discloses the oxidation of cycloaliphatic hydrocarbons in the liquid phase with a gas containing molecular oxygen and in the presence of about 10% water to produce two phases and avoid formation of esters.

U.S. Pat. No. 2,557,282 (Hamblet et al.) discloses production of adipic acid and related aliphatic dibasic acids; more particularly to the production of adipic acid by the direct oxidation of cyclohexane.

U.S. Pat. No. 2,439,513 (Hamblet et al.) discloses the production of adipic acid and related aliphatic dibasic acids and more particularly to the production of adipic acid by the oxidation of cyclohexane.

U.S. Pat. No. 2,223,494 (Loder et al.) discloses the oxidation of cyclic saturated hydrocarbons and more particularly to the production of cyclic alcohols and cyclic ketones by oxidation of cyclic saturated hydrocarbons with an oxygen-containing gas.

U.S. Pat. No. 2,223,493 (Loder et al.) discloses the production of aliphatic dibasic acids and more particularly to the production of aliphatic dibasic acids by oxidation of cyclic saturated hydrocarbons with an oxygen-containing gas.

German Patent DE 44 26 132 A1 (Kysela et al.) discloses a method of dehydration of process acetic acid from liquid-phase oxidation of cyclohexane with air, in the presence of cobalt salts as a catalyst after separation of the adipic acid after filtration, while simultaneously avoiding cobalt salt precipitates in the dehydration column, characterized in that the acetic acid phase to be returned to the beginning of the process is subjected to azeotropic distillation by the use of added cyclohexane, under distillative removal of the water down to a residual content of less than [sic] 0.3–0.7%.

PCT International Publication WO 96/03365 (Constantini et al.) discloses a process for recycling a cobalt-containing catalyst in a direct reaction of oxidation of cyclohexane into adipic acid, characterized by including a step in which the reaction mixture obtained by oxidation into adipic acid is treated by extraction of at least a portion of the glutaric acid and the succinic acid formed during the reaction.

U.S. Pat. No. 5,221,800 (Park et al.) discloses a process for the manufacture of adipic acid. In this process, cyclohexane is oxidized in an aliphatic monobasic acid solvent in the presence of a soluble cobalt salt wherein water is continuously or intermittently added to the reaction system after the initiation of oxidation of cyclohexane as indicated by a suitable means of detection, and wherein the reaction is conducted at a temperature of about 50° C. to about 150° C. at an oxygen partial pressure of about 50 to 420 pounds per square inch absolute.

U.S. Pat. No. 4,263,453 (Schultz et al.) discloses a process claiming improved yields by the addition of water at the beginning of the reaction, generally of the order of 0.5 to 15% relative to monobasic aliphatic acid solvent, and preferably 1 to 10% relative to the solvent.

U.S. Pat. No. 3,390,174 (Schultz et al.) discloses a process claiming improved yields of aliphatic dibasic acids when oxidizing the respective cyclic hydrocarbons at temperatures between 130° and 160° C., while removing the water of reaction substantially as quickly as it is formed.

None of the above references, or any other references known to the inventors disclose, suggest or imply, singly or in combination, removal of catalyst, from hydrocarbon reaction mixtures, preferably for recycling, subject to the intricate and critical controls and requirements of the instant invention as described and claimed.

Our U.S. Pat. Nos. 5,801,282; 5,580,531; 5,654,475; 5,558,842; and 5,502,245; our copending U.S. patent application Ser. No. 08/587,967 (filed Jan 17, 1996, now U.S. Pat. No. 5,883,292 issued Mar. 16, 1999, and PCT International publication WO 96/07056, all of which are incorporated herein by reference, describe methods and apparatuses relative to controlling reactions in atomized liquids.

Our U.S. Pat. Nos. 5,824,819; 5,817,868; and 5,801,273; and our co-pending U.S. patent application Ser. Nos. 08/812,847 filed on Mar. 6, 1997; Ser. No. 08/824,992, filed on Mar. 27, 1997, now U.S. Pat. No. 5,922,908 issued Jul. 13, 1999; Ser. No. 08/861,180, filed on May 21, 1997; Ser. No. 08/861,281, filed on May 21, 1997; Ser. No. 08/861,210, filed on May 21, 1997; Ser. No. 08/876,692, filed on Jun. 16, 1997; Ser. No. 08/900,323, filed on Jul. 25, 1997; Ser. No. 08/931,035, filed on Sep. 16, 1997; Ser. No. 08/932,875, filed on Sep. 18, 1997; Ser. No. 08/934,253, filed on Sep. 19, 1997, now U.S. Pat. No, 5,929,277 issued Jun. 27, 1999; Ser. No. 08/989,910, filed on Dec. 12, 1997; Ser. No. 08/986,505 filed Dec. 8, 1997, now U.S. Pat. No. 908,589 issued Jun. 1, 1999; 60/074,068 filed Feb. 9, 1998; 60/075,257 filed Feb. 19, 1998; 60/086,159 filed May 20, 1998; 60/086,118 filed May 20, 1998; 60/101,918 filed Sep. 24, 1998; 60/086,119 filed May 20, 1998; 60/091,483 filed Jul. 2, 1998; 60/093,256 filed Jul. 17, 1998; 60/091,796 filed Jul. 6, 1998; 60/105,048 filed Oct. 20, 1998; 60/111,848 filed Dec. 11, 1998; 60/110,206 filed Nov. 30, 1998; as well as concurrently filed "Methods and Devices for Treating Cobalt Catalyst in Oxidation Mixtures Resulting from Oxidation of Hydrocarbons to Dibasic Acids", (Attorney Docket No. 900105.423, Express Mail No. EM067732722US, U.S. patent application Ser. No. 091245,157, filed Feb. 4, 1999, are all also incorporated herein by reference.

All of our following PCT patent applications, are also incorporated herein by reference: PCT/US97/10830 filed on Jun. 23, 1997 (WO 97/49485); PCT/US97/12944 filed on Jul. 23, 1997 (WO 98/07677); PCT/US96/07056 filed May 17,1996 (WO 96/40610); PCT/US97/17684 filed Sep. 30, 1997 (WO 98/19789); PCT/US97/17812 filed Oct. 2, 1997 (WO 98/27029); PCT/US97/17883 filed Oct. 3, 1997 (WO 98/20966); PCT/US98/25105 filed Dec. 1, 1998; PCT/US98/19111 filed Sep. 14, 1998; PCT/US98/14506 filed Jul. 13, 1998; PCT/US98/19099 filed Sep. 16, 1998; PCT/US98/19057 filed Sep. 14, 1998.

SUMMARY OF THE INVENTION

As aforementioned, this invention relates to methods of oxidizing hydrocarbons, such as cyclohexane for example, to respective intermediate oxidation products, such as adipic acid for example, and more specifically, how to remove catalyst after the reaction, preferably for recycling. More particularly, this invention pertains a method of removing catalyst from a reaction mixture containing one or more dibasic acids, the reaction mixture having been formed after reaction of a hydrocarbon with an oxidant in the presence of the catalyst, water, and a monobasic acid solvent, in an oxidation zone, the method being characterized by steps of:

(a) precipitating a major part of the catalyst from the reaction mixture by removing water at least partially and/or controlling temperature to be adequately high for causing catalyst precipitation;

(b) removing the precipitated catalyst;

(c) further precipitating and removing a major part of remaining catalyst by at least partially removing the monobasic acid solvent and melting the one or more dibasic acids until catalyst precipitates;

(d) removing the catalyst which precipitates in step (c) leaving behind a filtrate containing a minor amount of catalyst; and (e) substantially removing from the filtrate the minor amount of catalyst.

This invention is also related to a method of removing catalyst from a reaction mixture containing one or more dibasic acids, the reaction mixture having been formed after reaction of a hydrocarbon with an oxidant in the presence of the catalyst, water, and a monobasic acid solvent, in an oxidation zone, the method being characterized by steps of:

(a) precipitating a major part of the catalyst from the reaction mixture by removing water at least partially and/or controlling temperature to be adequately high for causing catalyst precipitation;

(b) removing the precipitated catalyst;

(c) further removing remaining catalyst by a method selected from a group consisting of ion exchange, electrodialysis, catalyst precipitation with a base, catalyst precipitation with a salt, and a combination thereof.

Further, this invention pertains a method of treating a reaction mixture containing one or more dibasic acids, the reaction mixture having been formed after reaction of a hydrocarbon with an oxidant in the presence of the catalyst, water, and a monobasic acid solvent, in an oxidation zone, the method being characterized by steps of:

(a) precipitating a major part of the catalyst from the reaction mixture by removing water at least partially and/or controlling temperature to be adequately high for causing catalyst precipitation;

(b) removing the precipitated catalyst;

(c) further precipitating and removing a major part of remaining catalyst by at least partially removing the monobasic acid solvent and melting the one or more dibasic acids until catalyst precipitates;

(d) removing the catalyst which precipitates in step (c) leaving behind a filtrate containing dibasic acids and a minor amount of catalyst; and (e) at least partially precipitating and at least partially removing the one or more dibasic acids after step (d).

At least part of the minor amount of catalyst may be removed by miscellaneous methods, which include but are not limited to ion exchange, electrodialysis, precipitation with a base, precipitation with a salt, and a combination thereof.

The present invention is particularly applicable in the case that the hydrocarbon comprises a compound selected from a group consisting of cyclohexane, cyclohexanone, cyclohexanol, cyclohexylhydroperoxide, and a mixture thereof, the monobasic acid solvent comprises acetic acid, the catalyst comprises a cobalt compound, the oxidant comprises oxygen, and one of the dibasic acids comprises adipic acid.

The methods of the present invention may further comprise a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively. A step of spinning the polymer into fibers may also be used.

All ratios and percentages are expressed by weight unless otherwise specified.

A controller, preferably a computerized controller, may handle with ease and accuracy the operation of the devices of the present invention. Programming a computerized controller to perform such functions is a routine process, well known to the art. According to this invention, a controller, based on information received, from a reaction or oxidation zone, for example, controls feed rates of raw materials and/or recycled materials, temperatures, pressures, and other parameters in order to achieve the desirable results. The controller may also be programmed, by techniques well known to the art, to include flow sheet simulation, which may account for vapor/liquid equilibrium and energy balance effects.

As aforementioned, these methods and devices are particularly suited in case that the hydrocarbon comprises cyclohexane, the solvent comprises acetic acid, and the catalyst comprises a cobalt salt.

BRIEF DESCRIPTION OF THE DRAWING

The reader's understanding of this invention will be enhanced by reference to the following detailed description taken in combination with the drawing figure, wherein.

DETAILED DESCRIPTION OF THE INVENTION

Figure 1:
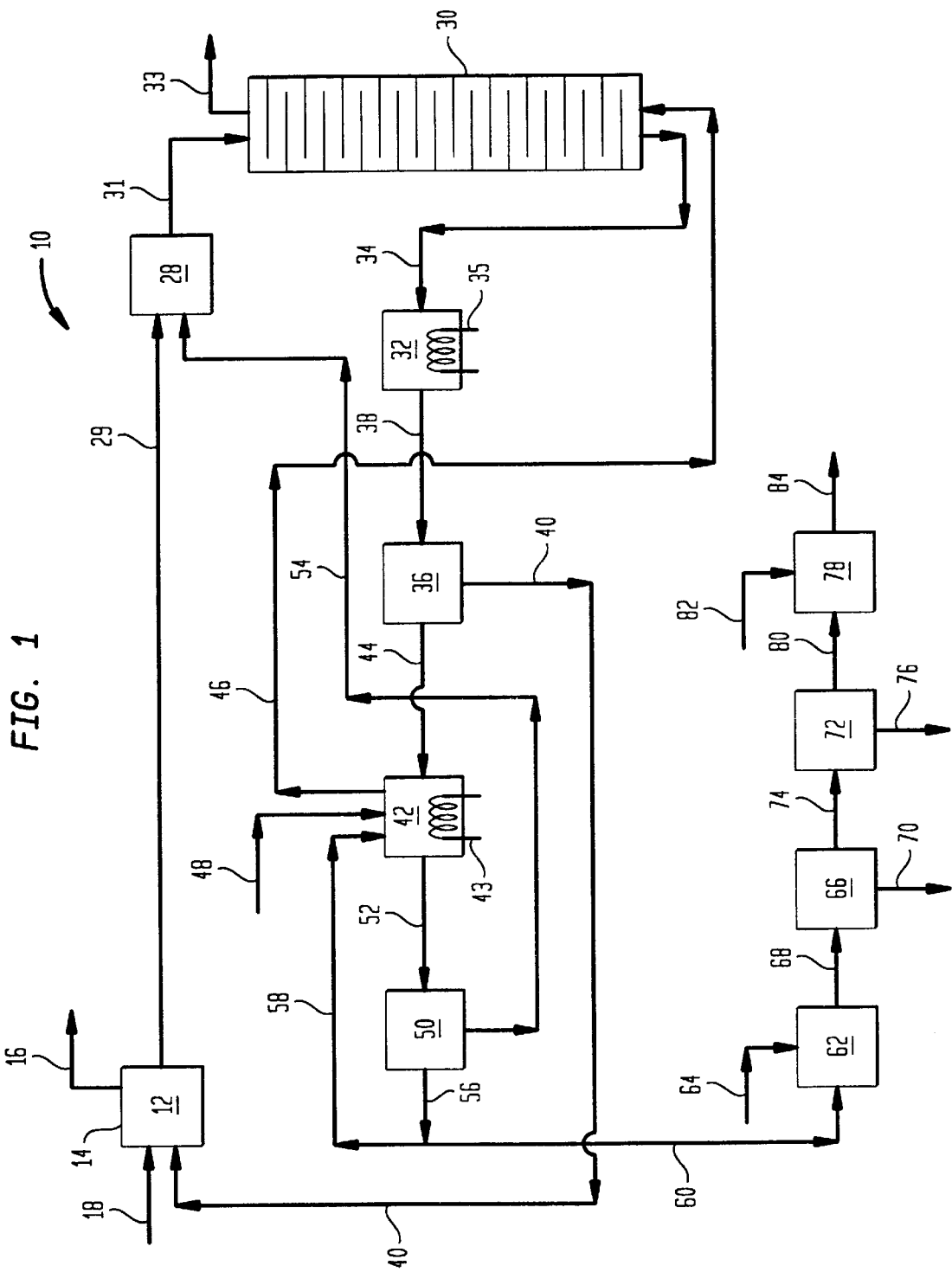
FIG. 1 illustrates a block diagram of a preferred embodiment of the present invention.

As aforementioned, this invention relates to methods and devices for oxidizing hydrocarbons, such as cyclohexane for example, to respective dibasic acids, such as adipic acid for example, and more specifically, how to remove catalyst after the reaction, preferably for recycling.

Proper catalyst handling in oxidation reactions has always been a considerable problem in the art. According to the present invention, catalyst is precipitated from the reaction mixture, after an oxidation has taken place, by a two stage and preferably by a three stage process, involving precipitation in a molten mixture containing dibasic acids, after partial catalyst precipitation caused by de-watering and/or thermal treatment. It is important that the molten mixture is adequately non-viscous for the catalyst separation. It was found by the inventors that addition of adjuncts in the molten mixture, such as glutaric acid for example, help in achieving workable viscosities. The final traces of catalyst may be removed at a third stage by ion exchange techniques, electrodialysis, etc.

Preferably, the catalyst which is precipitated from the molten mixture is recycled to the stage of de-watering and/or thermal treatment, as is explained in more detail herein, although it is possible to be recycled to the oxidation chamber, if so desired for some reason. Recycling of the precipitated catalyst to the stage of de-watering and/or thermal treatment presents enormous advantages, because the precipitated catalyst may be easily and efficiently recycled for repeated utilization, without substantial recycling of dibasic acids to the oxidation chamber.

De-watering is preferably conducted by use of distillation columns and/or addition of anhydrides, preferably acetic acid anhydride. However, other methods, such as for example use of other de-watering compounds, are not excluded and may be used very effectively, especially in combination with distillation columns. Examples of other de-watering compounds are colloidal silica, calcium oxide, molecular sieves, etc.

It has been found by the inventors that very important factors regarding partial catalyst precipitation in a reaction mixture are water level, catalyst level, hydrocarbon level, and temperature, among others, which include reaction products and by-products. For a given set of factors, partial catalyst precipitation is facilitated as the water level decreases, the catalyst level increases, the hydrocarbon level increases, and the temperature increases.

For better clarification of this invention, the examples given below assume that the hydrocarbon is cyclohexane, the intermediate oxidation product comprises adipic acid, the mixture contains a solvent comprising acetic acid, and the catalyst comprises a cobalt compound. It should be understood, however, that the teachings of this invention are applicable to different hydrocarbons, intermediate oxidation products, solvents, and catalysts than the ones used in the examples. Only minor modifications may be needed to fit each individual case.

Referring now to FIG. 1, there is depicted a reactor device or system 10, comprising an oxidation chamber 12 containing an oxidation zone 14. The reactor device 10 is only partially shown for demonstrating the components necessary to exemplify the present invention. Miscellaneous treatment, product or by-product separation, recycling, etc. devices, well known to the art, are not shown for purposes of clarity and brevity. Also devices connected to the oxidation reactor 12, such as for example distillation columns, condensers, re-boilers, etc., are not shown, also for purposes of brevity and clarity, and they are represented in this particular example by oxidation chamber exit line 16. The oxidation reactor 12 may be any type of reactor, such as for example stirred tank reactor, atomization reactor, recirculation reactor, etc.

Feeding means (for raw materials, miscellaneous recycled matter, gaseous oxidant, etc.) connected to the oxidation chamber 12 are represented by a single feeding line 18 for purposes of clarity and brevity. However, it should be understood that, in practice, a number of individual lines may be used, including if appropriate, devices such as for example mixing vessels, heaters, coolers, etc.

The oxidation chamber 12 is connected to a tank 28 through a transfer line 29. The tank 28 is in turn connected to a de-watering station 30 through transfer line 31. The de-watering station 30 leads to a thermal treatment station 32 through transfer line 34. The catalyst precipitation station 32 is preferably provided with a heater 35. The de-watering station 30 may be in the form of a distillation column 30, which column 30 is provided with an exit line 33, while the thermal treatment station 32 may be in the form of a heated tank. The distillation column may be provided with means, such as sweep arms for example to help prevent catalyst accumulation, in case catalyst precipitates within the column. It should be pointed out that the de-watering station and the thermal treatment station may be just one unit, or only one of the two stations may be required depending on the circumstances. If the water level of the contents of tank 28, for example, is low enough, heating the reaction mixture to a higher temperature in the thermal treatment station 32 (even in the absence of the de-watering station 30) may be adequate to cause precipitation of catalyst to a required degree. Similarly, if the temperature at the lower part of a distillation column is adequately high and the water level adequately low, precipitation of catalyst may occur. Further, addition of an anhydride, such as acetic acid anhydride for example, added to the de-watering station 30, or directly to the catalyst precipitation station 32, can lower the water level so that catalyst precipitates at the prevailing temperature inside the station 32. Our U.S. patent application Ser. No. 08/931,035, filed Sep. 16, 1997, now abandoned, gives a plurality of examples of such devices which may be used as the catalyst precipitation station 32.

Although not shown in the embodiment illustrated in FIG. 1, an oxidation station may be provided within transfer line 31, between tank 28 and de-watering column 30. In the oxidation station (not shown), cobalt ions being in valence II are oxidized to cobalt ions in valence III. This is useful in preventing any catalyst precipitation in column 30, as described in more detail in our copending U.S. patent application Ser. No. 08/986,505, filed on Dec. 8, 1997, now U.S. Pat. No. 5,908,589 issued Jun. 1, 1999 of David C. DeCoster, Eustathios Vassiliou, Mark W. Dassel, Ader M. Rostami, and Douglas J. Dudgeon, titled "Methods and Devices for Separating Catalyst from Oxidation Mixtures Containing Dibasic Acids", which is incorporated herein by reference. A reduction station may then be preferably incorporated in line 34 between the column 30 and the thermal treatment station or catalyst precipitation station 32 for reducing the cobalt ions from valence III to valance II, in order to promote catalyst precipitation at station 32, as also described in the same application.

The thermal treatment station 32 is connected to a catalyst separator 36 through transfer line 38. The catalyst separator 36 is provided with a solids removal line 40 which is preferably connected to the oxidation chamber 12. The catalyst separator 36 is also connected to a thermal treatment station 42 through a transfer line 44. The thermal treatment station 42, being provided with a heater 43, acts also as an evaporator for removing monobasic acid, such as acetic acid for example, through monobasic acid removal line 46. The thermal treatment station 42 may comprise more than one precipitation chambers, preferably arranged in series, if so desired. Although the monobasic acid removal line 46, may be connected to the oxidation chamber 12 for recycling the monobasic acid either as vapor or as liquid to said oxidation chamber 12, or to any other chamber, it is highly preferable that it is connected to the bottom of the de-watering station 30, in the case a column represents the de-watering station 30. In this manner, the heat contained in the monobasic acid, when removed from the thermal treatment station 42, can be used to drive column 30, at least partially. The station 42 is further provided with inlet line 48 for adding any desirable adjuncts, such as glutaric acid for example.

The thermal treatment station 42 is connected to a catalyst separator 50 through transfer line 52. The catalyst separator 50, which is a hot melt separator, is preferably connected to tank 28 through a solids removal line 54. It is also connected to a transfer line 56, which in turn is split into a recycle line 58 leading back to the thermal treatment station 42, and to a transfer line 60 leading to a dissolution station 62. A solvent line 64 is connected also to the dissolution station 62, which station is in turn connected to a dibasic acid precipitation and separation station 66, through transfer line 68.

The dibasic acid precipitation and separation station 66 is also connected to a solids removal line 70, and to a final catalyst removal station 72, through transfer line 74. The final catalyst removal station 72 is connected to a final catalyst removal line 76, and to a hydrolysis station 78 through transfer line 80. The hydrolysis station 78 is in turn connected to addition line 82 and to transfer line 84.

In operation of this embodiment, raw materials are fed through line 18 to the oxidation chamber 12, which encloses the oxidation zone 14. Oxidation chambers are well known to the art. According to this invention, in the case of adipic acid manufacture by direct oxidation of cyclohexane, the raw materials are preferably cyclohexane as the hydrocarbon; acetaldehyde or cyclohexanone as the initiator; oxygen, or air, or another gas mixture containing oxygen and inert gases such as nitrogen, as the oxidant; a cobalt compound as the catalyst; and acetic acid as the monobasic acid solvent. A small amount of water in the oxidation zone is preferably controlled to be higher than that at or under which catalyst precipitates, but lower than that at or over which a second liquid phase is formed. It is also preferable that the raw materials concentrations and the conditions are maintained at a steady state. By the term "steady state", it is meant that the reaction has reached an equilibrium, which equilibrium, however, may be adjusted periodically or continuously in order to achieve a desired result. If for example more water is needed in the reaction or oxidation zone to avoid catalyst precipitation, the water feed rate to the reaction or oxidation zone may be increased appropriately, and still the reaction may be considered to be at a "steady state." Similarly, if less water is needed to avoid formation of two phases, the water feed rate to the reaction or oxidation zone may be decreased appropriately, and still the reaction may be considered to be at a "steady state." The feed rates of the rest of the ingredients or raw materials are also managed in a similar way, whether they are newly introduced or they are products of recycling.

The liquid mixture exiting the oxidation chamber 12 enters tank 28 through transfer line 29. It comprises adipic acid, glutaric acid, succinic acid, acetic acid, and smaller amounts of cyclohexane, water, and other adjuncts, such as esters and other by-products. In tank 28, this liquid mixture is also mixed with catalyst solids from the catalyst separator 50 through the solids removal line 54, as better explained hereinbelow. Although the catalyst solids from the catalyst separator 50, may be treated in any desired way, in a manner to re-utilize the catalyst in the oxidation zone 14 of the oxidation chamber 12, it is desirable that the precipitated catalyst be recycled to tank 28. A major reason is that the separated catalyst in line 54 contains salts of the catalyst, cobalt for example, with dibasic acids, such as for example adipic, glutaric, and succinic acids, along with free dibasic acids, in the case of adipic acid manufacture. Since it is not desirable to recycle dibasic acids and dibasic acid salts back to the oxidation chamber 12, the solids removal line 54 preferably directs these solids to the tank 28. The precipitated solids from the catalyst separator 50 may first be washed with liquids (molten or otherwise) containing little or no dibasic acids (for example a portion of the stream carried through line 33 after condensation), in order for example to remove coexisting liquids, or for other reasons. Tank 28 contains an abundance of acetic acid along with smaller amounts of water and other matter, provided by the transfer line 29. Due to the acetic acid and water content in tank 28, the dibasic acid catalyst salts, which were insoluble in the molten dibasic acids in the thermal treatment station 42, are redissolved and re-equilibrated to form predominantly acetic acid salt of the catalyst metal in the contents of the tank 28.

In sequence, the contents of the tank 28 are transferred to the de-watering station 30, which preferably is in the form of a de-hydration column. As the contents of tank 28 move down the column, hot acetic acid, preferably coming from the thermal treatment station 42 via transfer line 46, removes gradually water and other minor components, such as for example cyclohexane, cyclohexanol, and cyclohexanone, through vapor line 33. The vapors removed through line 33, the great majority of which is monobasic acid, may be recycled, directly or as a condensate, to the oxidation chamber 12, or treated otherwise. The liquid mixture at the bottom of the column 30 is transferred to the thermal treatment station 32, after having been dehydrated to a desired degree. The higher the dehydration or de-watering degree, the higher the percentage of precipitated catalyst in the thermal treatment station 32 at a set temperature. Of course the set temperature has to be higher than a precipitation temperature at which catalyst precipitates, as described in detail in our copending U.S. Patent application Serial No. 08/931,035, filed Sep. 16, 1997 now abandoned.

It should be pointed out again that removal of water from a mixture includes binding the water in a manner that it is not free to act as water for the purposes of this invention. For example, reaction of an acid anhydride, such as acetic acid anhydride for example, with water contained in a mixture, is considered as water removal from the mixture, or de-watering, or dehydration, despite the fact the oxygen and hydrogen atoms, which constituted the reacted water molecule, are still present in the mixture.

Due to the abundance of monobasic acid, such as acetic acid for example, the major part of the precipitated catalyst at station 32 is in the form of a salt of the monobasic acid (cobaltous acetate, for example), which after separation in the catalyst separator 36, is preferably recycled to the oxidation zone 14 of the oxidation chamber 12, through the solids removal line 40. However, the precipitate may be washed with liquids containing little or no dibasic acids (for example a portion of the stream carried through line 33 after condensation), in order for example to remove liquids, or for other reasons. At this stage, it is preferable to precipitate the major portion of the dissolved catalyst. It is preferable to precipitate over 60%, more preferable over 70%, and even more preferable over 80%.

It is preferable to maintain the cobalt catalyst in valence III within the column to avoid catalyst precipitation within the column, but essential to maintain the cobalt in valence II, after the mixture leaves column 30 through line 34, in order to promote precipitation in chamber 32.

After separation of the precipitated catalyst in the catalyst separator 36, the remaining mixture, containing dissolved catalyst, dibasic acids, monobasic acid solvent, and small amounts of other adjuncts, is transferred to the thermal treatment station 42. At the thermal treatment station 42, which also acts as an evaporator for removing at least the major part of the monobasic acid solvent, such as acetic acid for example, substantially a major part of the rest of catalyst is precipitated, mainly as dibasic acid salts in molten dibasic acids containing also by-product esters and other minor adjuncts. The removed monobasic acid is preferably recycled to the bottom of the dehydration column 30 through line 46, as aforementioned, for driving the column. If for any reason, the monobasic acid solvent is not recycled as vapor to the dehydration column 30, a re-boiler, well known to the art, will be necessary to drive the column. A re-boiler may also be used in conjunction with the introduction of acetic acid through line 46, if necessary.

The thermal treatment station 42 may be operated at reduced pressure for more efficient evaporation of monobasic acid, or for other reasons. However, the pressure in the thermal treatment station 42 should be preferably maintained higher than the pressure in the de-watering station 30, to avoid compression requirements in line 46. The temperature in the thermal treatment station 42 is high enough to maintain its contents in a molten state. It is sometimes desirable to use inlet line 48 for adding into station 42 adjuncts, such as glutaric acid, for example, for lowering the melting point and viscosity of the contents of station 42.

As already discussed, monobasic acid anhydride, such as acetic acid anhydride for example, may be used in addition to or instead of the dehydration column 30, constituting the de-watering station. The catalyst precipitated in the thermal treatment station 42 is separated from molten liquid matter in the separator 50 and recycled to tank 28, as mentioned earlier. The molten liquid matter leaves the system through the line 56. Part of it is recycled to the thermal treatment station 42 though the recycle line 58, if so desired to reduce the viscosity of the contents of the thermal treatment station 42, and part of it is transferred to the dissolution chamber 62 through transfer line 60.

A solvent, such as for example water, or a mixture of water and acetic acid, or acetic acid, is introduced to the dissolution station 62. The solvent dissolves the molten liquid coming from the separation station 50. The quantity of solvent added, and the temperature inside the dissolution station 62 are such that preferably only a single-phase liquid prevails without any solid precipitate, for all practical purposes, in said dissolution station 62. The single-phase liquid is in turn transferred to the dibasic acid separation and precipitation station 66, where dibasic acid, adipic acid in this example, is precipitated by crystallization, and removed through the solids removal line 70. The crystallization may be conducted by lowering the temperature, or by other techniques well known to the art. Flash crystallization may be used. Flash crystallization may be achieved in one or more stages, wherein both temperature and pressure are reduced. The pressure may be reduced through vacuum pumps, condensers, and other accessories (not shown), well known to the art. Of course, flash crystallization may be augmented or replaced by conventional cooling techniques. The slurry produced by the precipitation of the adipic acid, is treated for separating the adipic acid from the liquid phase, and said adipic acid is removed through the solids removal line 70, as aforementioned. The removed adipic acid may then be recrystallized or otherwise treated. The most common methods of solids separation are centrifugation and filtration, well known to the art.

The liquid or filtrate, after removal of the adipic acid, is transferred through transfer line 74 to the final catalyst removal station 72, wherein minor amounts or final traces of catalyst are separated by using any technique well known to the art. Such techniques include but are not limited to utilization of ion exchange resins, electrodialysis, precipitation with bases, precipitation with salts, or other moieties, etc. precipitation with bases produces cobalt hydroxide, while a preferable salt is a soluble metal carbonate in order to produce cobalt carbonate.

After removal of the final minor amounts of catalyst, the filtrate is transferred to the hydrolysis station 78, wherein the miscellaneous by-product esters are hydrolyzed, by addition of hydrolyzing agents, such as for example strong acids or bases, through addition line 82. The hydrolyzed esters, along with dibasic acids (glutaric, adipic and succinic) and other by-product adjuncts, are transferred through transfer line 84 for further treatment and/or separation and/or recycling.

Some of the advantages that may be achieved, among others, by following respective teaching of this invention are:

The catalyst is precipitated in three stages.

In a first catalyst precipitation zone, preferably the majority of catalyst is precipitated by removing water and/or thermally treating the reaction mixture. This is advantageous for two main reasons. One reason is that the precipitated catalyst is largely in the form of a salt with the monobasic acid solvent (cobaltous acetate, for example), so that it may be recycled to the oxidation zone directly without simultaneous recycling of substantial quantities of other products or by-products (dibasic acids or their salts with the catalyst, for example). A second reason is that by removal of the majority of the catalyst in the first precipitation zone, a workable melt of reasonable viscosity is produced in the next catalyst separation zone, so that substantially all of the remaining catalyst may be separated easily and effectively, by hot melt filtration or hot melt centrifugation, for example. Without removal of the majority of the catalyst in the first catalyst precipitation zone, a highly viscous mixture of molten mass and catalyst solids is produced, from which catalyst separation is impractical, if not impossible.

Although the catalyst in a second catalyst separation zone is largely precipitated in the form of salts of catalyst with dibasic acids, recycling of this precipitated catalyst to the first catalyst precipitation zone, wherein there is an abundance of monobasic acid solvent (acetic acid, for example), causes a major part of the catalyst to be re-precipitated as a salt of the catalyst with the monobasic acid solvent (cobaltous acetate, for example), which may be recycled to the oxidation zone, as already mentioned, without substantial recycling of other products and by-products.

The monobasic acid solvent (acetic acid vapor, for example) removed from the second catalyst precipitation zone (by evaporation) may be recycled to the de-watering station of the first catalyst precipitation zone, which may contain a dehydration column, in a manner that it drives the column by providing at least part of the energy it consumed in order to be evaporated. After it removes water in the dehydration column, it may be recycled to the oxidation zone, if so desired.

The small amounts or traces of catalyst remaining, after the aggressive separation of catalyst by precipitation described above, may be removed by techniques which are effective and efficient for removal of metals in dilute solutions. Such techniques include separation by ion exchange, precipitation after addition of compounds forming insoluble bases or salts of the catalyst metal, electrodialysis, etc.

It should be understood that according to the present invention, any liquids or gases or off-gases may be recycled totally or partially from any section to any other section, if so desired. Further, any combinations of the exemplifying matter, in part or in total, or any equivalent arrangements or any combinations of equivalent arrangements may be utilized, and are within the scope of the present invention.

Although miscellaneous functions are preferably controlled by a computerized controller, it is possible, according to this invention, to utilize any other type of controller or even manual controls and/or labor for controlling one or more functions. Preferred computerized controllers are artificially intelligent systems (expert systems, neural networks, and fuzzy logic systems, well known to the art). Of the three types of the artificially intelligent systems, the neural network, which is a learning system, collects information from different places of the device (for example pressure, temperature, chemical or other analysis, etc.), stores this information along with the result (pressure drop rate, reaction rate, reactivity, and the like, for example), and is programmed to use this information in the future, along with other data if applicable, to make decisions regarding the action to be taken at each instance. The expert systems are programmed based on the expertise of experienced human beings. The fuzzy logic systems are based on intuition rules in addition to expertise rules.

Oxidations according to this invention, are non-destructive oxidations, wherein the oxidation product is different than carbon monoxide, carbon dioxide, and a mixture thereof, such as adipic acid for example. Of course, small amounts of these compounds may be formed along with the oxidation product, which may be one product or a mixture of products.

Examples include, but of course, are not limited to preparation of C5–C8 aliphatic dibasic acids from the corresponding saturated cycloaliphatic hydrocarbons, such as for example preparation of adipic acid from cyclohexane. Other examples include preparation of aromatic carboxylic acids such as benzoic acid, phthalic acid, isophthalic acid, and terephthalic acid, among others.

Regarding adipic acid, the preparation of which is especially suited to the methods and apparatuses of this invention, general information may be found in a plethora of U.S. Patents, among other references. These include, but are not limited to: U.S. Pat. Nos. 2,223,493; 2,589,648; 2,285,914; 3,231,608; 3,234,271; 3,361,806; 3,390,174; 3,530,185; 3,649,685; 3,657,334; 3,957,876; 3,987,100; 4,032,569; 4,105,856; 4,158,739 (glutaric acid); U.S. Pat. Nos. 4,263,453; 4,331,608; 4,606,863; 4,902,827; 5,221,800; and 5,321,157.

Dibasic acids (for example adipic acid, phthalic acid, isophthalic acid, terephthalic acid, and the like) or other suitable compounds may be reacted, according to well known to the art techniques, with a reactant selected from a group consisting of a polyol, a polyamine, and a polyamide in a manner to form a polymer of a polyester, or a polyamide, or a (polyimide and/or polyamideimide), respectively. Preferably the polyol, the polyamine, and the polyamide are mainly a diol, a diamine, and a diamide, respectively, in order to avoid excessive cross-linking. The polymer resulting from this reaction may be spun by techniques well known to the art to form fibers.

Examples demonstrating the operation of the instant invention have been given for illustration purposes only, and should not be construed as limiting the scope of this invention in any way. In addition it should be stressed that the preferred examples discussed in detail hereinabove, as well as any other examples encompassed within the limits of the instant invention, may be practiced individually, or in any combination thereof, according to common sense and/or expert opinion. Individual sections of the examples may also be practiced individually or in combination with other individual sections of examples or examples in their totality, according to the present invention. These combinations also lie within the realm of the present invention. Furthermore, any attempted explanations in the discussion are only speculative and are not intended to narrow the limits of this invention.

What is claimed is:

1. A method of removing catalyst from a reaction mixture containing one or more dibasic acids, the reaction mixture having been formed after reaction of a hydrocarbon with an oxidant in the presence of the catalyst, water, and a monobasic acid solvent, in an oxidation zone, the method being characterized by steps of:

(a) precipitating a major part of the catalyst from the reaction mixture by removing water at least partially and/or controlling temperature to be adequately high for causing catalyst precipitation;

(b) removing the precipitated catalyst;

(c) further precipitating and removing a major part of remaining catalyst by at least partially removing the monobasic acid solvent and melting the one or more dibasic acids until catalyst precipitates;

(d) removing the catalyst which precipitates in step (c) leaving behind a filtrate containing a minor amount of catalyst; and (e) substantially removing from the filtrate the minor amount of catalyst.

2. A method as defined in claim 1, wherein at least part of the minor amount of catalyst is removed by first precipitating at least part of the minor amount of catalyst with a base or salt, and then separating any precipitated catalyst.

3. A method as defined in claim 1, wherein at least part of the minor amount of catalyst is substantially removed by a process selected from the group of electrodialysis, ion exchange, and a combination thereof.

4. A method as defined in claim 1, wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, the catalyst comprises a cobalt compound, the oxidant comprises oxygen, and one of the dibasic acids comprises adipic acid.

5. A method as defined in claim 2, wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, the catalyst comprises a cobalt compound, the oxidant comprises oxygen, and one of the dibasic acids comprises adipic acid.

6. A method as defined in claim 3, wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, the catalyst comprises a cobalt compound, the oxidant comprises oxygen, and one of the dibasic acids comprises adipic acid.

7. A method as defined in claim 1, wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

8. A method as defined in claim 7, further comprising a step of spinning the polymer into fibers.

9. A method as defined in claim 4, wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

10. A method as defined in claim 9, further comprising a step of spinning the polymer into fibers.

11. A method as defined in claim 5, wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

12. A method as defined in claim 11, further comprising a step of spinning the polymer into fibers.

13. A method as defined in claim 6, wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

14. A method as defined in claim 13, further comprising a step of spinning the polymer into fibers.

15. A method of removing catalyst from a reaction mixture containing one or more dibasic acids, the reaction mixture having been formed after reaction of a hydrocarbon with an oxidant in the presence of the catalyst, water, and a monobasic acid solvent, in an oxidation zone, the method being characterized by steps of:
   (a) precipitating a major part of the catalyst from the reaction mixture by removing water at least partially and/or controlling temperature to be adequately high for causing catalyst precipitation;
   (b) removing the precipitated catalyst;
   (c) further removing remaining catalyst by a method selected from a group consisting of ion exchange, electrodialysis, catalyst precipitation with a base, catalyst precipitation with a salt, and a combination thereof.

16. A method as defined in claim 15, wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, the catalyst comprises a cobalt compound, the oxidant comprises oxygen, and one of the dibasic acids comprises adipic acid.

17. A method as defined in claim 15, wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

18. A method as defined in claim 17, further comprising a step of spinning the polymer into fibers.

19. A method as defined in claim 16, wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

20. A method as defined in claim 19, further comprising a step of spinning the polymer into fibers.

21. A method of treating a reaction mixture containing one or more dibasic acids, the reaction mixture having been formed after reaction of a hydrocarbon with an oxidant in the presence of the catalyst, water, and a monobasic acid solvent, in an oxidation zone, the method being characterized by steps of:
   (a) precipitating a major part of the catalyst from the reaction mixture by removing water at least partially and/or controlling temperature to be adequately high for causing catalyst precipitation;
   (b) removing the precipitated catalyst;
   (c) further precipitating and removing a major part of remaining catalyst by at least partially removing the monobasic acid solvent and melting the one or more dibasic acids until catalyst precipitates;
   (d) removing the catalyst which precipitates in step (c) leaving behind a filtrate containing dibasic acids and a minor amount of catalyst; and
   (e) at least partially precipitating and at least partially removing the one or more dibasic acids after step (d), before or after a step of removing the minor amount of catalyst.

22. A method as defined in claim 21, the minor amount of catalyst is removed by a process selected from a group consisting of ion exchange, electrodialysis, catalyst precipitation with a base, catalyst precipitation with a salt, and a combination thereof.

23. A method as defined in claim 21, wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, the catalyst comprises a cobalt compound, the oxidant comprises oxygen, and one of the dibasic acids comprises adipic acid.

24. A method as defined in claim 22, wherein the hydrocarbon comprises a compound selected from a group consisting of cyclohexane, cyclohexanone, cyclohexanol, cyclohexylhydroperoxide, and a mixture thereof, the monobasic acid solvent comprises acetic acid, the catalyst comprises a cobalt compound, the oxidant comprises oxygen, and one of the dibasic acids comprises adipic acid.

25. A method as defined in claim 21, wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

26. A method as defined in claim 25, further comprising a step of spinning the polymer into fibers.

27. A method as defined in claim 22, wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

28. A method as defined in claim 27, further comprising a step of spinning the polymer into fibers.

29. A method as defined in claim 23, wherein the method further comprises a step of reacting at least one of the dibasic acids with a reactant selected from a group consisting of a polyol, a polyamine, and a polyamide in a manner to form a polymer of a polyester, or a polyamide, or a (polyimide and/or polyamideimide), respectively.

30. A method as defined in claim 29, further comprising a step of spinning the polymer into fibers.

* * * * *